United States Patent [19]
Fukuda et al.

[11] Patent Number: 5,331,178
[45] Date of Patent: Jul. 19, 1994

[54] OPTICAL SURFACE INSPECTING SYSTEM FOR INSPECTING THE SURFACE OF A ROLLING ROLL HAVING MECHANISM FOR KEEPING CLEAN A WINDOW THROUGH WHICH A CAMERA DETECTS A CONDITION OF THE ROLLING ROLL

[75] Inventors: Makoto Fukuda; Makoto Azuma; Katsuro Dejima; Yukiyoshi Maeda; Kunihiko Yoshitake, all of Kakogawa, Japan

[73] Assignee: Kabushiki Kaisha Kobe Seiko Sho, Kobe, Japan

[21] Appl. No.: 980,792

[22] PCT Filed: May 14, 1992

[86] PCT No.: PCT/JP92/00617
§ 371 Date: Mar. 3, 1993
§ 102(e) Date: Mar. 3, 1993

[87] PCT Pub. No.: WO93/01488
PCT Pub. Date: Jan. 21, 1993

[30] Foreign Application Priority Data

Jul. 5, 1991 [JP] Japan .................................. 3-165648

[51] Int. Cl.⁵ .............................................. G01N 21/89
[52] U.S. Cl. ..................................... 250/571; 250/239; 250/572
[58] Field of Search ................ 250/562, 563, 571, 572, 250/573, 239; 356/429, 430, 431

[56] References Cited

U.S. PATENT DOCUMENTS 4,266,142  5/1981  Crawford ........................... 250/572

FOREIGN PATENT DOCUMENTS 55-12322   4/1980  Japan .
59-174204 10/1984  Japan .
63-29237   2/1988  Japan .
64-15951   1/1989  Japan .
1-295108  11/1989  Japan .
0038952    2/1990  Japan ................................. 250/572

Primary Examiner—David C. Nelms
Assistant Examiner—John R. Lee
Attorney, Agent, or Firm—Oblon, Spivak, McClelland, Maier & Neustadt

[57] ABSTRACT

An optical surface inspecting system in accordance with the present invention forms still pictures of the surface of a rolling roll while the rolling roll is rotating. The optical surface inspecting system comprises a housing box provided with a window in its front wall, a stroboscopic illuminating device contained in the housing box, a television camera contained in the housing box, and a water droplet removing mechanism combined with the housing box. The water droplet removing mechanism removes droplets of cooling water scattered on the surface of the window, so that the television camera is able to pick up accurate images of the surface of the rolling roll while the rolling roll is rotating.

7 Claims, 4 Drawing Sheets

Work roll  Depressions

OPTICAL SURFACE INSPECTING SYSTEM FOR INSPECTING THE SURFACE OF A ROLLING ROLL HAVING MECHANISM FOR KEEPING CLEAN A WINDOW THROUGH WHICH A CAMERA DETECTS A CONDITION OF THE ROLLING ROLL

DESCRIPTION

1. Technical Field

The present invention relates to an optical surface inspecting system for optically inspecting the surface condition of a rolling roll for rolling a steel plate or the like and, more particularly, to an optical surface inspecting system capable of taking a still picture of the surface (circumference) of a rolling roll during rolling operation to enable the observation and inspection of the surface condition of the rolling roll.

2. Background Art

When finishing a steel plate by hot rolling on a finishing mill, mill scales adhere to the surface of the work roll of the roughing stands of the hot finishing mill. The mill scales have minute hexagonal cracks. Under some rolling condition, the scales fall off the work roll and form circumferential bands of depressions, called "roll bandings" in the surface of the work roll as shown in FIG. 7. If the work roll having such roll bandings is used for rolling a steel plate, projections corresponding to the depressions of the work roll are formed in the surface of the steel plate, and the projections are crushed by the work roll of the other stands of the finishing mill to form scale pits in the steel plate.

Accordingly, the finishing mill is stopped at appropriate intervals, the work roll is removed from the finishing stand, the surface of the work roll is inspected visually and, if the surface is roughened by flaws, such as roll bandings, that will possibly form scale pits or if the surface is roughened to an extent that will form roll bandings, the work roll is replaced with another work roll.

A method of evaluating the surface roughness of a roll is proposed in Japanese Patent Laid-open (Kokai) No. 1-295108. This known method measures the distance between a predetermined position and the circumference of a roll by a ultrasonic distance meter, calculates radii of the roll at measuring points, determines the profile (the shape) of the roll, and evaluates the surface roughness of the roll from the profile.

The visual inspection of the surface of a roll requires the roll to be removed from the rolling mill and to be set in place on the rolling mill after inspection, which needs much time and labor. Moreover, if the rolling operation is interrupted for the inspection of the roll, the rolling mill needs to be kept at an idle for warming up the rolls before resuming the rolling operation, which reduces the productivity of the rolling mill. On the other hand, the method of evaluating the surface roughness of a roll from the profile of the roll has difficulty in accurately detecting minute roll bandings of a surface roughness Ra on the order of several microns.

The present invention has been made in view of the foregoing problems and it is therefore an object of the present invention to provide an optical surface inspecting system for inspecting the surface of a rolling roll, capable of taking a still picture of the surface of the rolling roll while the rolling roll is rotating even if the surface of the rolling roll is wetted with cooling water to cool the rolling roll properly, and of enabling the accurate inspection of the surface of the rolling roll through the observation and evaluation of the still picture of the surface of the rolling roll.

SUMMARY OF THE INVENTION

An optical surface inspecting system for inspecting the surface of a rolling roll in accordance with the present invention comprises: a housing box capable of moving in the direction of length of the rotating rolling roll being sprayed with cooling water or wetted with residual cooling water, and having a transparent window and a water removing mechanism for removing droplets of the cooling water from the outer surface of the window; a stroboscopic illuminating device contained in the housing box to illuminate the surface of the rolling roll through the window; a television camera contained in the housing box, operated in synchronism with the illuminating operation of the stroboscopic illuminating device to convert the surface of the rotating rolling roll into corresponding still video signals representing a still picture of the surface of the rolling roll; an image storage device for storing the still video signals provided by the television camera; a display for displaying a picture represented by the still video signals stored in the image storage device; and a controller capable of synchronizing the illuminating operation of the stroboscopic illuminating device and the image pickup operation of the television camera by a synchronizing signal, and of controlling operation for storing the still video signals representing the surface of the rolling roll provided by the television camera in the image storage device and operation for sending the still video signals to the display.

The water removing mechanism employed in the optical surface inspecting system of the present invention may be such as capable of blowing compressed air supplied from an air source against the outer surface of the window, or such as provided with a water column forming device having a water column forming nozzle joined to the window and capable of forming a water column between the surface of the rolling roll and the window when water is supplied thereto by pressure.

When the optical surface inspecting system is provided with the water column forming nozzle, the water column forming nozzle may be such as formed of a transparent material or may be such as comprising a tubular guide member having one end fixed to the housing box, a nozzle body having a spout and axially slidably put on the guide member, and an elastic member extended between the nozzle body and the window of the housing box to bias the nozzle body elastically forward so as to enable the nozzle body to be moved backward by a predetermined distance from the surface of the rolling roll by repulsive force which results when pressure water is spouted through the nozzle body.

LIST OF REFERENCE CHARACTERS

Figure 1:
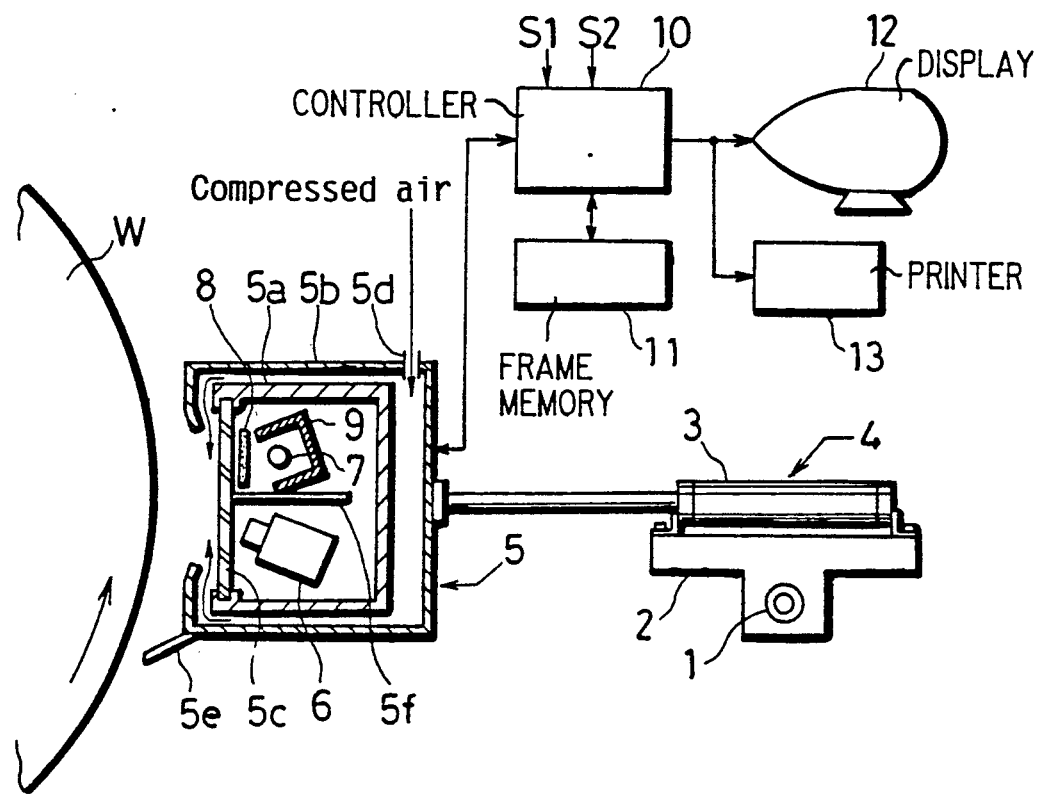
FIG. 1 is a schematic, partly sectional view of an optical surface inspecting system for optically inspecting the surface of a rolling roll, in a first embodiment according to the present invention.

| 1 | Feed screw | 2 | Traveling base |
|---|---|---|---|
| 3 | Pneumatic actuator | 4 | Moving unit |
| 5 | Housing box | 5a | Inner case |
| 5b | Outer case | 5c | Glass plate |
| 5d | Air inlet | 6 | CCD camera |
| 7 | Xenon lamp | 10 | Controller |
| 11 | Frame memory | 12 | CRT display |
| 13 | Printer | 21 | Housing box |
| 21c | Glass plate | 22 | Annular xenon lamp |
| 23 | Water column forming nozzle unit | | |
| 23a | Pressure pipe | 30 | Guide member |
| 30a | Flange | 30b | Pressure pipe |
| 31 | Nozzle body | 31a | Shoulder |
| 31b | Skirt | 32 | Coil spring |
| 33 | Water column forming nozzle unit | | |
| W | Rolling roll | | |

BEST MODE FOR CARRYING OUT THE INVENTION

An optical surface inspecting system for inspecting the surface of a rolling roll, in accordance with the present invention has a housing box internally provided with a stroboscopic illuminating device and a television camera, moved longitudinally of the rolling roll, and positioned at a predetermined inspecting position. A controller controls the television camera and the stroboscopic illuminating device for synchronous operation by a synchronizing signal. The television camera picks up the image of the surface of the rotating rolling roll through a window formed on the housing box and converts the image of the surface of the rolling roll into a still video signal. The still video signal provided by the television camera is stored in an image storage device. A display displays a still picture of the surface of the rolling roll represented by the still video signal stored in the image storage device. Thus, the still picture of the surface of the rolling roll can be formed while the rolling roll is rotating to enable the observation and inspection of the surface condition of the rolling roll.

Basically, the optical surface inspecting system of the present invention is intended to enable the observation and inspection of the surface of the rolling roll even if the rolling roll is rotating. Therefore, it is possible that the accuracy of the observation and inspection of the surface of the rolling roll is deteriorated by scattered droplets of cooling water sprayed on the surface of the rolling roll for cooling. When observing and inspecting the surface of the rolling roll while the rolling roll is rotating, (1) cooling water is sprayed on the surface of the rolling roll while the rolling roll is rotating or (2) spraying cooling water is stopped temporarily and the rolling roll rotates with the surface thereof wetted with residual cooling water. In either case, scattered droplets of cooling water hinder the observation and inspection of the surface of the rolling roll.

Accordingly, the optical surface inspecting system of the present invention is provided with a water removing mechanism for removing droplets of cooling water from the outer surface of the window to solve problems attributable to scattered droplets of cooling water.

The optical surface inspecting system of the present invention may be provided with a water removing mechanism capable of removing scattered droplets of cooling water by spraying compressed air supplied from an air source against the outer surface of the window. The water removing mechanism removes droplets of cooling water scattered by the rotating rolling roll on the outer surface of the window even if cooling water sprayed on the rolling roller to cool the same immediately before taking the picture of the surface of the rolling roll remains on the surface of the rolling roll and, consequently, a clear still picture of the surface of the rolling roll can be obtained. However, the accurate observation and inspection of the surface of the rolling roll is impossible even if the optical surface inspecting system is provided with such a water removing mechanism if cooling water is sprayed continuously on the surface of the rolling roll, because the surface of the rolling roll is coated with foul cooling water. The accurate observation and inspection of the surface of the rolling roll is impossible also when the surface of the rolling roll is coated with foul cooling water even if cooling water is not sprayed continuously on the surface of the rolling roll.

The inventors of the present invention made studies to enable accurate observation and inspection of the surface of the rolling roll under such difficult conditions and have found that problems attributable to cooling water can be solved by a water removing mechanism having a water column forming nozzle having a spout communicating with the window of the housing box, and capable of forming a water column between the window and the rolling roll when pressure water is supplied thereto. When pressure water is supplied to the water column forming nozzle, the window of the housing box and the surface of the rotating rolling roll wetted by cooling water are interconnected by a water column when pressure water is supplied into the water column forming nozzle, illuminating light emitted by the stroboscopic illuminating device travels through the window and the water column, and illuminates the surface of the rolling roll, reflected light reflected by the surface of the rolling roll travels through the water column and the window and falls on the television camera. Thus, troubles attributable to scattered droplets of cooling water or foul cooling water coating the surface of the rolling roll can be eliminated and a still picture of the surface of the rotating rolling roll can be obtained even if cooling water is sprayed on the surface of the rolling roll. Furthermore, separated from foul cooling water, the surface of the window of the housing box is never polluted by foul cooling water. Still further, the accurate observation and inspection of the surface of the rolling roll can be achieved by the optical surface inspecting system provided with the water column forming mechanism even if spraying cooling water is interrupted temporarily during the inspection of the surface of the rolling roll while the rolling roll is rotating, the surface of the rolling roll is coated with foul cooling water or cooling water remaining on the surface of the rolling roll is scattered in droplets, because the surface of the rolling roll is washed by pressure water forming the water column.

As mentioned above the water column forming nozzle of the water column forming mechanism may be formed of a transparent material. When such a transparent water column forming nozzle is employed, light emitted by the stroboscopic illuminating device travels through the water column and falls on the surface of the rolling roll, part of the illuminating light is refracted at the inner and outer surface of the water column forming nozzle, travels through the water column forming nozzle and falls on the surface of the rolling roll, and reflected light reflected by the surface of the rolling roll travels through the water column and the water column forming nozzle and falls on the television camera, which brings about additional effects that the difference in brightness between the central region and peripheral region of the illuminated area in the surface of the rolling roll enables the optical surface inspecting system to form a generally bright, clear, conspicuous still picture having a three-dimensional effect. A suitable transparent material for forming the water column forming nozzle is, for example, an acrylic resin.

As mentioned above, another possible water column forming nozzle comprises a tubular guide member having one end fixed to the housing box, a nozzle body having a spout and axially slidably put on the guide member, and an elastic member extended between the nozzle body and the window of the housing box to bias the nozzle body elastically forward so as to enable the nozzle body to be moved backward by a predetermined distance from the surface of the rolling roll by the pressure of pressure water when pressure water is supplied to the nozzle body. This water column forming nozzle has the following additional effects. When pressure water is supplied to the water column forming nozzle and spouted through the spout, the nozzle body having the spout is moved backward by a predetermined distance by repulsive force which results when pressure water is spouted against the surface of the rolling roll to a position where the resilience of the elastic member balances the repulsive force, and the nozzle body stops stably with a predetermined interval between the nozzle body and the surface of the rolling roll. When the shape of the nozzle body and the pressure of the pressure water are fixed, the nozzle body can be held with the least possible space between the front end of the nozzle body and the surface of the rotating rolling roll so that the front end thereof may not come into contact with the surface of the rolling roll by employing an elastic member having an appropriate elastic property, which surely prevents the unstable image pick up operation due to the disturbance of the water column by sprayed cooling water.

Preferred embodiments of the present invention will be described hereinafter.

First Embodiment

Referring to FIG. 1 showing an optical surface inspecting system in a first embodiment according to the present invention for inspecting the surface of a rolling roll, indicated at W is a work roll (hereinafter referred to "rolling roll") of the second finishing stand F2, not shown, of a hot finishing mill for hot-rolling a steel plate. A moving unit 4 is disposed between the rolling roll and the rolling roll, not shown, of the third finishing stand F3. The moving unit 4 comprises a feed screw 1 extended in parallel to the longitudinal axis of the rolling roll W and driven for rotation in opposite directions by a motor, not shown, a traveling base 2 mounted on the feed screw 1 so as to be driven by the feed screw 1 for movement along the longitudinal axis of the rolling roll W according to the rotation of the feed screw 1, and a pneumatic actuator 3 mounted on the traveling base 2. A housing box 5 is attached to the free end of the piston rod of the pneumatic actuator 3. The piston rod is stretched out toward and retracted away from the surface of the rolling roll W.

As shown in FIG. 1, the housing box 5 comprises a box-like inner case 5a having a window paned with a transparent glass plate 5c on the front wall thereof facing the rolling roll W, and a box-like outer case 5b containing the inner case 5a with a space between their walls and having an opening formed in the front wall thereof facing the rolling roll W. The outer case 5b is provided with an air inlet port 5d. Compressed air is supplied from an air source, not shown, through the air inlet port 5d into the space between the inner case 5a and the outer case 5b. A splash guard 5e is attached to the lower end of the front wall outer case 5b.

The inner case 5a of the housing box 5 contains a CCD camera (CCD television camera) 6 having with a plurality of CCDs (charge coupled devices) arranged in a two-dimensional arrangement and provided with a lens system having a small numerical aperture, a long focal length and a large depth of focus and consisting of a plurality of lenses, and a stroboscopic illuminating device comprising a xenon lamp 7, a diffusing plate 8, such as a ground glass plate, disposed in front of the xenon lamp 7 to diffuse the light emitted by the xenon lamp 7, and a screen plate 9 disposed behind the xenon lamp 7. The stroboscopic illuminating device and the CCD camera 6 are separated from each other by a partition plate 5f.

Upon receiving an inspection start signal S1 from an external device, a controller 10 turns on the xenon lamp 7 in synchronism with a vertical synchronizing signal for the CCD camera 6, stores a still video signal representing an image of the surface of the rolling roll W provided by the CCD camera 6 in a frame memory 11, i.e., an image storage device. Upon receiving a display signal S2, the controller 10 sends the still video signal from the frame memory 11 to a CRT display 12, i.e., an image display. A printer 13 is connected to the controller 10. The controller 10, the frame memory 11, the CRT display 12 and the printer 13 are placed in an inspection room.

The operation of the optical surface inspecting system will be described hereinafter. The surface of the rolling roll W is inspected in the spare time between the passage of a steel plate through the hot finishing mill and the start of rolling operation for the next steel plate. Cooling water is stopped and the rotating speed of the rolling roll W is reduced the surface speed from a working surface speed in the range of 200 to 300 m/min to a surface speed on the order of 150 m/min. Then, the motor, not shown, rotates the feed screw 1 to move the traveling bed 2 along the longitudinal axis of the rolling roll W to an inspecting position. Then, the pneumatic actuator 3 is actuated so that the piston rod is stretched out to position the housing box 4 near the rolling roll W.

In this state, the inspector operates the external device to give an inspection start signal S1 to the controller 10, and then the controller 10 turns on the xenon lamp 7 for a predetermined time in synchronism with a vertical synchronizing signal for the CCD camera 6 and the CCD camera 6 provides a still video signal representing the image of the surface of the rotating rolling roll W.

Compressed air for purging is blown out through the space around the glass plate 5c of the housing box 5 to purge droplets of cooling water scattered by the rotating rolling roll W and wetting the glass plate 5c so that a clear image of the surface of the rolling roll W can be formed. Since the lens system of the CCD camera 6 has a large depth of focus, the image formed by the CCD camera is not blurred even if the rolling roll W shakes.

The controller 10 stores the still video signal provided by the CCD camera 6 in the frame memory 11. The housing box 5 is moved along the longitudinal axis of the rolling roll W and is positioned sequentially at predetermined inspecting positions, and the CCD camera 6 picks up an image of the surface of the rotating rolling roll W at each inspecting position.

After completing the operation for picking up images of the surface of the rolling roll W, the inspector operates the external device to give a display signal S2 to the controller 10. Then, the still video signals representing picture frames, stored in the frame memory 11 are read sequentially and are displayed on the CRT display 12 in still pictures. The inspector observes and inspects the still pictures displayed on the CRT display 12 to evaluate the surface condition of the rolling roll W.

Figure 2:
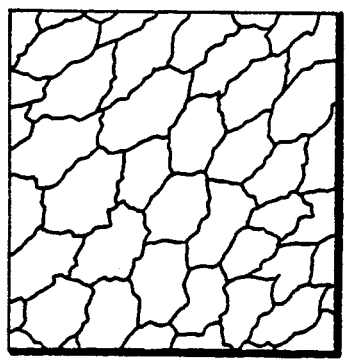
FIGS. 2(a) and 2(b) are sketches of pictures of the surface of a rolling roll, obtained by the optical surface inspecting system of FIG. 1.
Figure 2:
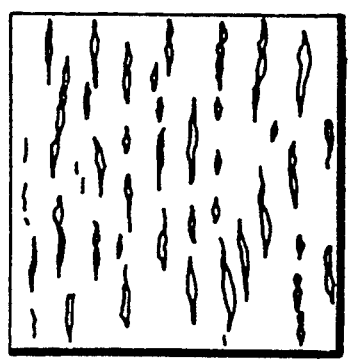

FIGS. 2(a) and 2(b) are sketches of the still pictures of the surface of the rolling roll obtained by the optical surface inspecting system of the present invention. As is evident from FIGS. 2(a) and 2(b), the optical surface inspecting system is capable of clearly showing minute hexagonal cracks in scales (FIG. 2 (a)) adhering to the surface of the rolling roll, and roll bandings (FIG. 2(b)) formed in the surface of the rolling roll by the scales fallen off the rolling roll.

Since the housing box 5 of the optical surface inspecting system is provided with water removing mechanism for purging water droplets from the surface of the glass plate 5c of the window, clear still pictures of the surface of the rolling roll W can be obtained even if cooling water sprayed on the rolling roll W to cool the same before starting the surface inspecting operation remains on the surface of the rolling roll W and droplets of cooling water are scattered on the glass plate 5c by the rotating rolling roll W, because the droplets of cooling water are purged from the glass plate 5c of the window.

Second Embodiment

Figure 3:
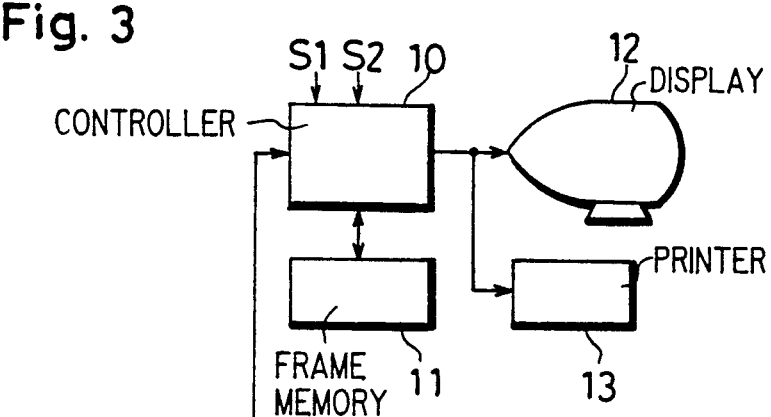
FIG. 3 is a schematic, partly sectional view of an optical surface inspecting system for inspecting the surface of a rolling roll, in a second embodiment according to the present invention.
Figure 3:
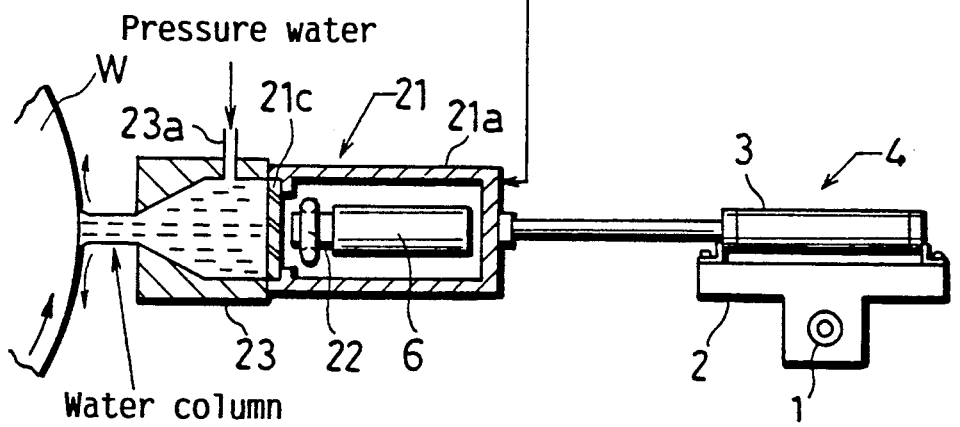

An optical surface inspecting system in a second embodiment according to the present invention is shown in FIG. 3, in which parts like or corresponding to those shown in FIG. 2 are denoted by the same reference characters and the description thereof will be omitted.

Referring to FIG. 3, a housing box 21 is fixedly held on the free end of the piston rod of a pneumatic actuator 3 included in a moving unit 4. The housing box 21 comprises a box-like case 21a and a transparent glass plate 21c fitted in a window formed in the front wall of the case 21a facing a rolling roll W. The housing box 21 contains a CCD camera 6, and an annular xenon lamp 22 included in a stroboscopic illuminating device.

A cylindrical water column forming nozzle 23 having a spout and formed of an acrylic resin is attached to the front wall of the housing box 21 provided with the glass plate 21c to form a water column between the glass plate 21c and the surface of the rolling roll W when pressure water is supplied into the water column forming nozzle 23. A pressure water supply pipe 23a is connected to the water column forming nozzle 23 to supply pressure water from a water source, not shown, into the water column forming nozzle 23. The inner space of the water column forming nozzle 23 is tapered toward the spout.

The operation of the optical surface inspecting system thus constructed will be described hereinafter. The surface of the rolling roll W is inspected in a spare time between the passage of a steel plate through the hot finishing mill and the start of rolling operation for the next steel plate. During the surface inspecting operation, cooling water is sprayed continuously on the rolling roll W and the rolling roll W is rotated at the working surface speed on the order of 200 m/min. The surface of the rolling roll W was observed and inspected by the same procedure as that carried out by the optical surface inspecting system in the first embodiment.

Pressure water is supplied into the water column forming nozzle 23 to form a water column between the glass plate 21c of the housing box 21 and the surface of the rotating rolling roll W being sprayed with cooling water. Illuminating light emitted by the xenon lamp 22 travels through the glass plate 21c of the housing box 21 and the water column and illuminates the surface of the rolling roll W. Reflected light reflected by the surface of the rolling roll W travels through the water column and the glass plate 21c and falls on the television camera 6. Thus, a still picture of the surface of the rotating rolling roll W can be obtained even if cooling water is sprayed on the rolling roll W during the surface inspecting operation. Since foul cooling water is unable to reach the glass plate 21c of the housing box 21, the glass plate 21c will not be polluted.

Figure 4:
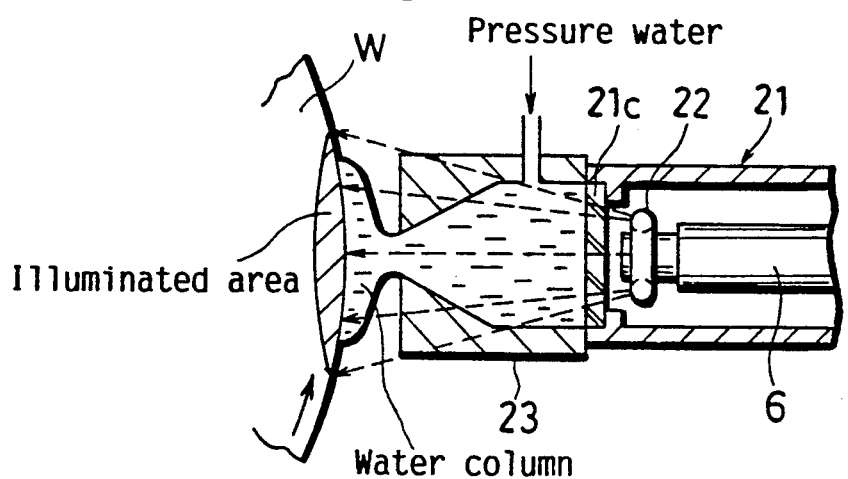
FIG. 4 is a sectional view of a water column forming nozzle employed in the optical surface inspecting system of FIG. 3, showing a mode of illuminating the surface of a rolling roll.

Since the water column forming nozzle 23 is formed of a transparent acrylic resin, illuminating light emitted by the xenon lamp 22 travels through the water column and falls on the surface of the rolling roll W, while part of the illuminating light is refracted at the inner and outer circumferences of the water column forming nozzle 23, is transmitted through the water column forming nozzle 23 and falls on the surface of the rolling roll W as shown in FIG. 4. Consequently, reflected light travels through the water column and the water column forming nozzle 23 and falls on the television camera 6. In FIG. 4, the mode of refraction of light is not illustrated.

The transparent water column forming nozzle, as compared with an iron or aluminum water column forming nozzle which intercepts light, enables the more effective illumination of the central region and peripheral region of the illuminated area in different degree of brightness, which enables the optical surface inspecting system to form a generally bright, clear and conspicuous still picture having a three-dimensional effect. The still picture of such a satisfactory quality makes possible the precise inspection of the surface condition of the rolling roll W. For example, a water column forming nozzle of an acrylic resin having a diameter of 38 mm forms an illuminated area of a diameter of about 60 mm on the surface of the rolling roll W.

Third Embodiment

Figure 5:
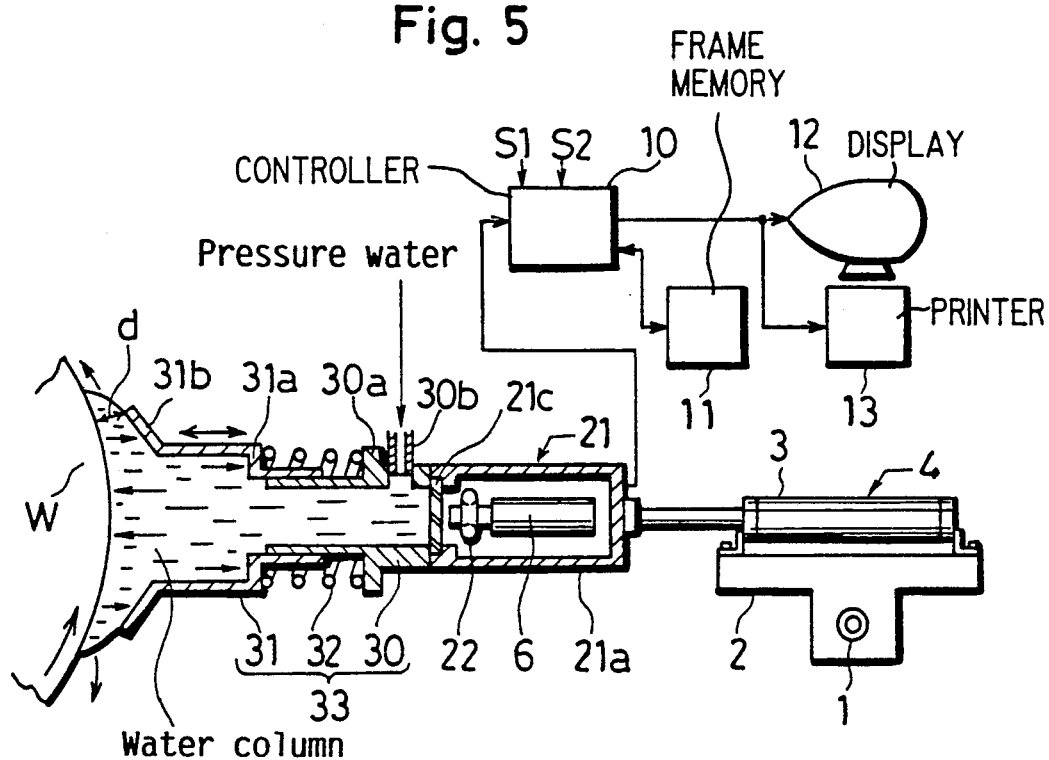
FIG. 5 is a schematic, partly sectional view of an optical surface inspecting system for inspecting the surface of a rolling roll, in a third embodiment according to the present invention.
Figure 6:
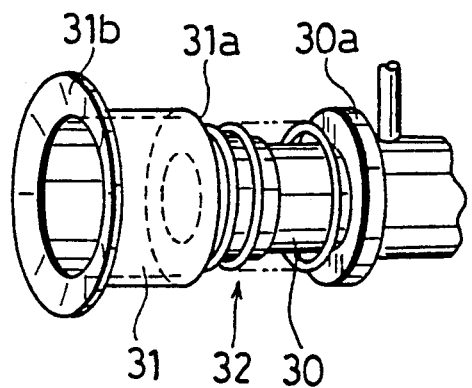
FIG. 6 is a perspective view of a water column forming nozzle unit employed in the optical surface inspecting system of FIG. 5.
Figure 7:
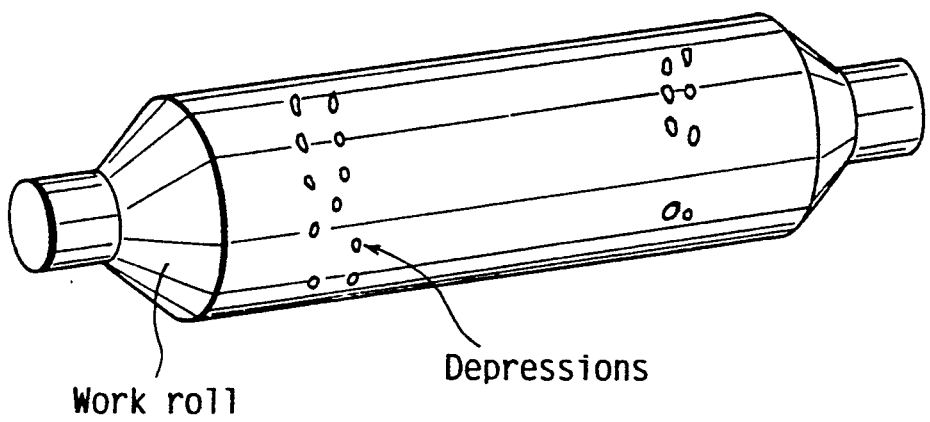
FIG. 7 is a perspective view of assistance in explaining roll bandings formed on a work roll.

FIG. 5 shows an optical surface inspecting system in a third embodiment according to the present invention and FIG. 6 shows a water column forming nozzle employed in the optical surface inspecting system of FIG. 5 in a perspective view. This optical surface inspecting system is the same in construction as the optical surface inspecting system of FIG. 3, except that the construction of a water column forming nozzle employed in this optical surface inspecting system is different from that of the water column forming nozzle of the optical surface inspecting system of FIG. 3. In FIG. 5, parts like or corresponding to those shown in FIG. 3 are denoted by the same reference characters and the description thereof will be omitted.

Referring to FIGS. 5 and 6, a housing box 21, similarly to the housing box shown in FIG. 3, contains a CCD camera 6 and an annular xenon lamp 22 included in a stroboscopic illuminating device. The housing box 21 is provided with a window paned with a glass plate 21c in the front wall thereof. A cylindrical guide member 30 has one end closely attached to the front wall of the housing box 21. The guide member 30 has a flange 30a formed in one end thereof near the glass plate 21c. A pressure water supply pipe 30b through which pressure water is supplied into the guide member 30 is connected to the guide member 30.

A nozzle body 31 having a spout forms a water column between the surface of a rolling roll W and the glass plate 21c of the window of the housing box 21 when pressure water is supplied therein. As shown in FIGS. 5 and 6, the nozzle body 31 has a larger cylindrical portion and a smaller cylindrical portion, and a shoulder 31a is formed between the larger and smaller cylindrical portions. A skirt 31b expanding forward is formed on the front end of the larger cylindrical portion nearer to the rolling roll. The smaller cylindrical portion of the nozzle body 31 is put on the guide member 30 having one end fixed to the housing box 21 so as to be axially slidably on the guide member 30.

A coil spring 32, i.e., an elastic member, is put on the guide member 30 so as to extend between the flange 30a of the guide member 30 and the shoulder 31a of the nozzle body 31 to bias the nozzle body 31 forward. The coil spring 32 allows the nozzle body 31 to be moved away by a predetermined distance from the surface of the rolling roll W by the repulsive force of pressure water spouted through the spout against the surface of the rolling roll W. The guide member 30, the nozzle body 31 and the coil spring 32 constitute a water column forming nozzle 33.

The operation of the optical surface inspecting system thus constructed will be described hereinafter. The rolling roll W finished by roll grinding is mounted on the second stand F2, not shown, of a hot finishing mill. The feed screw 1 is rotated by a motor, not shown, to move the traveling bed 2 along the longitudinal axis of the rolling roll W to a first inspecting position. Then, the piston rod of the pneumatic actuator 3 is stretched out to advance the housing box 21 provided with the water column forming nozzle 33 toward the rolling roll W to position the housing box 21 so that the housing box 21 is advanced toward the rolling roll W so that the front end of the nozzle body 31 comes into contact with the surface of the rolling roll W and is moved backward slightly relative to the guide member 30 against the resilience of the coil spring 32. Then, pressure water is supplied into the water column forming nozzle 33 to form a water column between the surface of the rolling roll W and the glass plate 21c of the window of the housing box 21.

The repulsive force of the pressure water spouted through the spout acts mainly on the skirt 31b of the nozzle body 31 and the inner surface of the shoulder 31a to move the nozzle body 31 backward by a predetermined distance. The backward movement of the nozzle body 31 stops when the repulsive force balances the resilience of the coil spring 32 and the nozzle body 31 is positioned with a space of a predetermined width d between the front end of the nozzle body 31 and the surface of the rolling roll W. For example, it is possible to position the nozzle body 31 with a space of a predetermined width d of about 1 mm between the front end of the nozzle body 31 and the surface of the rolling roll W by supplying pressure water of a pressure in the range of 2 to 3 kg/cm$^2$ by selectively determining the spring constant of the coil spring 32.

After the housing box 21 has been positioned with the space of the predetermined width d between the front end of the nozzle body 31 and the surface of the rolling roll W, the rolling roll W is rotated at a surface speed on the order of 200 m/min to start hot finish rolling a steel plate and cooling water is sprayed on the rolling roll W. During the hot finish rolling operation, the nozzle body 31 is held so that the space of the predetermined width d is maintained.

After the hot finish rolling has been continued for a predetermined time, the inspector gives an inspection start signal S1 to the controller 10. Then, the controller 10 turns on the annular xenon lamp 22 for a predetermined time in synchronism with a vertical synchronizing signal for the CCD camera 6, and the CCD camera picks up an image of the surface of the rotating rolling roll W sprayed with cooling water and gives a still video signal representing the surface of the rolling roll W to the controller 10.

The traveling bed 2 is shifted along the longitudinal axis of the rolling roll W and positioned sequentially at inspecting positions. After the completion of the image pick-up operation, the inspector gives a display signal S2 to the controller 10. Then, the still video signals representing frames are read sequentially from the frame memory 11 and still pictures corresponding to the still video signals are displayed on the CRT display 12. The inspector observes and inspects the still pictures displayed on the CRT display 12 to evaluate the surface condition of the rolling roll W.

The nozzle body 31 having the spout of the water column forming nozzle 33 is able to slide axially toward and away from the rolling roll W, the coil spring 32 biases the nozzle body 31 forward so that the nozzle body 31 is able to be moved backward by the repulsive force of pressure water spouted through the spout of the nozzle body 31 and the nozzle body 31 is positioned with a space of a predetermined width between the front end of the nozzle body 31 and the surface of the rolling roll W.

Accordingly, the front end of the nozzle body 31 never comes into contact with the surface of the rotating rolling roll wetted by cooling water sprayed thereon and the nozzle body 31 can be held so that the width d of the space between the front end of the nozzle body 31 and the surface of the rolling roll is as small as about 1 min. Therefore, it does not occur that many bubbles are formed in the water column due to the disturbance of the water column by cooling water, so that failure in picking up an image of the surface of the rolling roll due to the disturbance of the water column by cooling water sprayed on the rolling roll can be surely prevented and still pictures precisely showing the surface condition of the rolling roll including minute hot cracks formed in scales produced during rolling operation can be obtained. Even if the rolling roll W is replaced with another rolling roll of a diameter different from that of the former, accurate adjustment of the width of the space between the water column forming nozzle 33 and the surface of the rolling roll is not necessary because the nozzle body 31 having the spout is moved backward by the repulsive force of the pressure water supplied into the water column forming nozzle 33 as far as the resilience of the coil spring 32 balances the repulsive force, which curtails time necessary for picking up images of the surface of the rolling roll.

The stroboscopic illuminating device need not be limited to those employed in the foregoing embodiments, provided with the xenon lamps 7 and 22 disposed within the housing box 5 and 21, respectively. For example, an optical surface inspecting system of the present invention may employ a stroboscopic illuminating device comprising a xenon lamp mounted on the moving bed 2 of the traveling unit 4, and a plurality of optical fibers having light emitting ends arranged on a circle around the CCD television camera 6 so as to emit light toward the glass plate 5c or 21c, and light receiving ends connected to the xenon lamp by an adapter.

CAPABILITY OF EXPLOITATION IN INDUSTRY

An optical surface inspecting system of the present invention has a housing box provided with a window, containing a stroboscopic illuminating device and a television camera, and provided with a water droplet removing mechanism for removing water droplets from the surface of the window. Accordingly, droplets of cooling water scattered on the surface of the window can be removed from the window, so that still pictures accurately showing the surface condition of the rolling roll can be obtained while the rolling roll is rotating.

Accordingly, the present invention makes unnecessary work for removing the rolling roll from and mounting the same on the rolling mill, which is necessary for the conventional visual inspection of the surface of the rolling roll. Furthermore, the optical surface inspecting system capable of obtaining accurate information about the process of roughening of the surface of the rolling roll enables the elucidation of the relation between the process of fatigue of the rolling load and rolling load, which is useful for planting a pass schedule so that roll bandings may not be formed and for significantly reducing scale pits.

We claim:

1. An optical surface inspecting system for inspecting the surface of a rolling roll, comprising:
 a housing box capable of moving along the longitudinal axis of a rotating rolling roll being sprayed with cooling water or coated with residual cooling water, provided with a window and a water droplet removing mechanism for removing droplets of cooling water adhering to the surface of the window by blowing compressed air, supplied from an air source, from at least two different directions against the surface of the window;
 a stroboscopic illuminating device contained in the housing box to illuminate the surface of the rolling roll through the window;
 a television camera contained in the housing box to pick up an image of the surface of the rolling roll in synchronism with the illuminating operation of the stroboscopic illuminating device and for providing a still video signal representing the image of the surface of the rolling roll;
 an image storage device for storing the still video signal provided by the television camera;
 an image display for displaying a picture corresponding to the still video signal stored in the image storage device; and
 a controlled which synchronizes the illuminating operation of the stroboscopic illuminating device with a vertical synchronizing for the television camera, stores the still video signal provided by the television camera in the image storage device and reads the still video signal from the image storage device and applies the same to the image display.

2. An optical inspecting system for inspecting a surface of a rolling roll being sprayed with water or coated with residual cooling water, comprising:
 a housing box;
 a window mounted on the housing box;
 a light source, mounted in the housing box, for irradiating light onto the rolling roll;
 a camera, mounted in the housing box, for collecting images of the rolling roll, irradiated by the light source, through the window; and
 water removing means, mounted to the housing box, for blowing air from at least two different directions to keep the water from the rolling roll off of the window.

3. An optical inspecting system for inspecting a surface of a rolling roll being sprayed with water or coated with residual cooling water, comprising:
 a housing box;
 a window mounted on the housing box;
 a light source, mounted in the housing box, for irradiating light onto the rolling roll;
 a camera, mounted in the housing box, for collecting images of the rolling roll, irradiated by the light source, through the window;
 a water column forming nozzle, mounted to the housing box nd connected to a pressurized water source, having a neck and water ejection orifice, a diameter of the water ejection orifice being smaller than a diameter of the neck, the water column forming nozzle spraying a water column into the roll, the camera collecting images of the rolling roll through the water column.

4. A system according to claim 3, wherein the water column forming nozzle is formed of a transparent material such that light from the light source illuminates the rolling roll through the water ejecting orifice and through the transparent material of the nozzle.

5. A system according to claim 4, wherein a diameter of the water column forming orifice is 38 mm and a diameter of illumination of the rolling roll by the light source is approximately 60 mm.

6. A system according to claim 3, wherein:
 said housing box moves along a longitudinal axis of the rolling roll;
 said light source is a stroboscopic light source;
 said camera collects images represented by still video signals;

said system further comprising:
- an image storage device for storing the still video signals provided by the television camera;
- an image display for displaying pictures corresponding to the still video signals stored in the image storage device; and
- a controller which synchronizes the operations of the light source with a vertical synchronization signal for the television camera, stores the still video signals provided by the camera in the image storage device and reads the still video signals from the image storage device and applies the read still video signals to the image display.

7. An optical surface inspecting system for inspecting the surface of a rolling roll, comprising:
- a housing box capable of moving along the longitudinal axis of a rotating rolling roll being sprayed with cooling water or coated with residual cooling water, provided with a window and a water droplet removing mechanism for removing droplets of cooling water adhering to the surface of the window;
- a stroboscopic illuminating device contained in the housing box to illuminate the surface of the rolling roll through the window;
- a television camera contained in the housing box to pick up an image of the surface of the rolling roll in synchronism with the illuminating operation of the stroboscopic illuminating device and for providing a still video signal representing the image of the surface of the rolling roll;
- an image storage device for storing the still video signal provided by the television camera;
- an image display for displaying a picture corresponding to the still video signal stored in the image storage device; and
- a controller which synchronizes the illuminating operation of the stroboscopic illuminating device with a vertical synchronizing signal for the television camera, stores the still video signal provided by the television camera in the image storage device, and reads the still video signal from the image storage device and applies the same to the image display;
- wherein said water droplet removing mechanism comprises a water column forming nozzle made of a transparent material, the water column forming nozzle having a spout attached to a front wall provided with the window of said housing box and for forming a water column between the window and the surface of the rolling roll when pressurized water is supplied into the water column forming nozzle.

* * * * *